United States Patent
Farcy et al.

(10) Patent No.: US 9,179,845 B2
(45) Date of Patent: Nov. 10, 2015

(54) SHARP FIBROUS NEEDLE PROBE FOR THE IN-DEPTH OPTICAL DIAGNOSTICS OF TUMOURS BY ENDOGENOUS FLUORESCENCE

(75) Inventors: René Alfred Farcy, Verrieres le Buisson (FR); Lama Al Chab, Gif sur Yvette (FR); Guillaume Dupuis, Paris (FR); Marie-Pierre Fontaine-Aupart, Fresnes (FR)

(73) Assignees: Université Paris-Sud, Orsay (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/384,496

(22) PCT Filed: Jul. 20, 2010

(86) PCT No.: PCT/FR2010/051533
§ 371 (c)(1),
(2), (4) Date: Jan. 17, 2012

(87) PCT Pub. No.: WO2011/010063
PCT Pub. Date: Jan. 27, 2011

(65) Prior Publication Data
US 2012/0116234 A1    May 10, 2012

(30) Foreign Application Priority Data
Jul. 20, 2009    (FR) ...................................... 09 55033

(51) Int. Cl.
*A61B 6/08*    (2006.01)
*A61B 5/00*    (2006.01)
(Continued)

(52) U.S. Cl.
CPC ............. *A61B 5/0084* (2013.01); *A61B 5/0071* (2013.01); *A61B 5/0075* (2013.01);
(Continued)

(58) Field of Classification Search
None
See application file for complete search history.

(56) References Cited

U.S. PATENT DOCUMENTS

| 4,269,192 A | 5/1981 | Matsuo | |
|---|---|---|---|
| 4,469,109 A * | 9/1984 | Mehl | ............................ 600/566 |

(Continued)

FOREIGN PATENT DOCUMENTS

| EP | 0 483 618 | 5/1992 |
|---|---|---|
| EP | 0 513 986 | 11/1992 |

(Continued)

OTHER PUBLICATIONS

Zbigniew Palasz et al., "Investigation of Normal and Malignant Laryngeal Tissue by Autofluorescene Imaging Technique", *Auris Nasus Larynx*, vol. 30, 2003, pp. 385-389.

*Primary Examiner* — Long V Le
*Assistant Examiner* — Farshad Negarestan
(74) *Attorney, Agent, or Firm* — Greer, Burns & Crain, Ltd.

(57) ABSTRACT

An optical sharp fibrous needle probe includes an optical fiber in a hollow needle ending in a cutting point. The optical fiber is inserted and bonded in the hollow of the needle and then polished to take on the exact needle cutting shape. The material to be explored is pricked by the needle. A light injection and recovery device is placed at the inlet of the fiber. The material located at the sharp end of the needle backscatters the incident light and generates an endogenous fluorescence signal. A part of this luminous flux is recovered by the point of the needle and sent back to the injection and recovery device. The same analyses the light in strength, duration and wavelength and enables a diagnostics without taking the in-depth explored material. An optical telemeter placed on the outer tip of the needle enables the depth of the explored area to be known.

16 Claims, 5 Drawing Sheets

(51) Int. Cl.
  *A61B 5/06* (2006.01)
  *A61B 5/1455* (2006.01)
  *A61B 5/1459* (2006.01)
  *G01N 21/47* (2006.01)
  *G01N 21/64* (2006.01)
  *A61B 19/00* (2006.01)
  *G01J 3/02* (2006.01)

(52) U.S. Cl.
  CPC ............... *A61B5/0091* (2013.01); *A61B 5/061* (2013.01); *A61B 5/1459* (2013.01); *A61B 5/14556* (2013.01); *A61B 5/4312* (2013.01); *A61B 5/6848* (2013.01); *A61B 5/6886* (2013.01); *G01N 21/474* (2013.01); *G01N 21/4795* (2013.01); *G01N 21/645* (2013.01); *G01N 21/6486* (2013.01); *A61B 5/0068* (2013.01); *A61B 2019/462* (2013.01); *A61B 2562/0242* (2013.01); *G01J 3/0278* (2013.01)

(56) References Cited

U.S. PATENT DOCUMENTS

| | | | |
|---|---|---|---|
| 4,566,438 | A | 1/1986 | Liese et al. |
| 5,303,026 | A | 4/1994 | Strobl |
| 5,562,100 | A | 10/1996 | Kittrell |
| 5,638,394 | A * | 6/1997 | Kim et al. .................. 372/68 |
| 6,088,106 | A * | 7/2000 | Rockseisen ............. 356/623 |
| 6,409,666 | B1 * | 6/2002 | Ito ............................ 600/439 |
| 6,633,367 | B2 * | 10/2003 | Gogolla .................. 356/5.15 |
| 7,428,048 | B1 | 9/2008 | Farkas et al. |
| 2003/0045798 | A1 * | 3/2003 | Hular et al. ............. 600/476 |
| 2004/0073119 | A1 * | 4/2004 | Mycek et al. ........... 600/476 |
| 2005/0027199 | A1 | 2/2005 | Clarke |

FOREIGN PATENT DOCUMENTS

| | | |
|---|---|---|
| EP | 0 635 238 | 1/1995 |
| WO | WO 92/14399 | 9/1992 |
| WO | WO 03/020119 | 3/2003 |
| WO | WO 2006/000704 | 1/2006 |
| WO | WO 2006/044973 | 4/2006 |
| WO | WO 2008/020130 | 2/2008 |
| WO | WO 2008/068685 | 6/2008 |

* cited by examiner

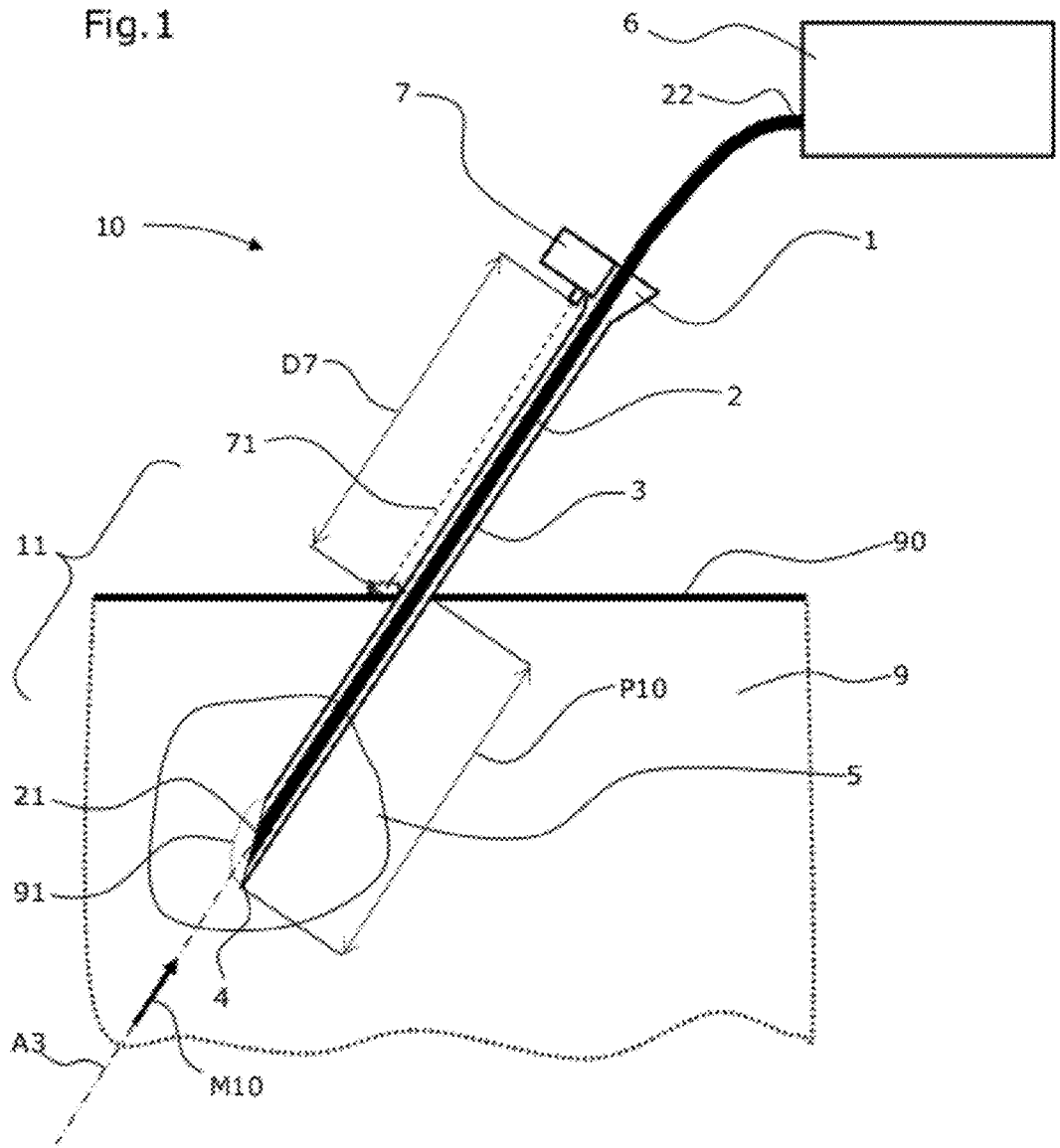

SHARP FIBROUS NEEDLE PROBE FOR THE IN-DEPTH OPTICAL DIAGNOSTICS OF TUMOURS BY ENDOGENOUS FLUORESCENCE

The present invention relates to a device for the in vivo observation or diagnostics of a compact biological tissue or living organ, enabling the endogenous fluorescence of the tissue to be measured using a subcutaneous optical probe. This device comprises a probe including a sharp point needle surrounding an optical fibre connected to a light injection and recovery device for measuring the backscattering of the injected light and the endogenous fluorescence generated by tissues under the effect of this injected light.

FIELD AND STATE OF THE ART

For the diagnostics of a tumour, for example in the case of the breast, a first step is often the discovery of a suspect lump by palpation or an abnormal spot on a routine screening mammography. These initial methods are cheap and have no or little risk for health, and can thus be commonly and easily practised in an ambulatory and medical office environment. In the case of such an alert, further tests are necessary to have more certainty about the nature of the discovered abnormality, in particular to assess the probability that it is a malignant or benign tumour, or even a simple cyst. Such further tests enable a decision to be made as regards the necessity and nature of a treatment, whether it is for example an ablation surgery, chemotherapy or radiation therapy treatment.

Now, the further tests currently available, even though they are less heavy than treatments, give themselves rise to constraints, costs and inconveniences. It is usually general imaging tests often based on irradiating radiations possibly with injections of labelling materials which are themselves irradiating, for example a scintigraphy. It can also be invasive tests such as a biopsy by taking a sample from the concerned tissues to perform a histological analysis of the suspect part in a laboratory.

These types of tests are often costly and require going to a specialized environment as regards general imaging. The samplings further require most often an invasive treatment or even an operation, which also gives rise to trauma and requires specific and restricting surgical conditions. The constraints related to these further tests are such that they only are practised beyond some suspicion threshold.

It is thus interesting to be able to perform simpler and cheaper tests as soon as possible after the discovery of an alert, allowing a first selection among the different cases of alert, and under less restricting and more systematic conditions.

In the case of internal organs, optical tests are carried out through endoscopy, through natural tracts or by a catheter introduced in vessels or arteries, which enable the nature of external cells of the targeted organ to be analysed through spectroscopy. These systems, sometimes called optical biopsy systems, use probes comprising a beam of optical fibres to convey light from inside the body to the operator or a recording apparatus, and thus to obtain an image in two dimensions of the surface of the observed organ, such as for example in document WO/2006/000704.

These multifibre systems sometimes use techniques for measuring the fluorescence of cells under a light excitation, as for example in document U.S. Pat. Nos. 5,562,100 or 5,303,026. Other apparatuses use imaging probes which contact the outer surface of organs, or which remain slightly remote from this surface as in document WO/2008/020130 which describes a fibre coming off the probe to partially penetrate into a pulmonary alveolus to view the inner walls thereof.

However, from outside the body as in endoscopy, there are few simple solutions allowing an analysis of tissues located inside, that is behind the mucosa of a compact organ such as a lymph node, or inside the wall, that is between the mucosae of a hollow organ such as the heart or lungs, or simply behind the epidermis such as a muscle or a breast.

Some optical instruments have been developed, which are provided to be sunk into tissues and perform different analyses. For that, document EP 0 483 618 can be cited, which describes a needle containing a transparent plastic enabling blood colour to be viewed on the proximal side when penetrating a vein.

Some documents such as U.S. Pat. Nos. 4,566,438, 4,269,192, WO 9214399A1 describe a sharp needle integrating several optical fibres to analyse a tissue. Patent EP0635238 integrates a single mode fibre in a partially transparent pointed probe to carry out an Optical Coherence Tomography (OCT) or patent US20050027199 inserting fibres in sharp tools again for performing OCT measurements. Patent WO 2008068685 describes a device consisting of a multifibre probe integrated in a biopsy needle for spectroscopy, patent EP 0513986 provides an integrated fibre device in a sharp probe for measuring the exogenous fluorescence induced by light sensitizers (photofrin) in a tumour. Patent WO 03/020119 A2 describes a deep set subcutaneous multisensor multifibre needle device for performing measurements of diffusion, $pO_2$, absorption spectrometry, electrical impedance and temperature.

All these devices use complex and costly analytical means, which restricts the diffusion possibilities of the system.

None of the above described subcutaneous needle devices neither provides nor allows for detecting the very low endogenous fluorescence signal of the tumour satisfactorily, in particular in a device with a very low diameter such as that of the thinnest needles (23G and 25G gauge). Their use is thus as invasive as a biopsy, and have thus little interest in a use prior to a biopsy, for example for screening or a confirmation when in doubt upon interpretation of a screening radiology.

Furthermore, these apparatuses have a probe structure which is often too complex to be easily sterilized in autoclave. Now the complexity of these probes is such that they cannot considered as disposable due to their production cost, in particular with the aim of a screening or preoperative test used on a very large population.

One object of the invention is to provide means and methods enabling simpler, quicker and cheaper tests to be performed, for example in screening complementary to the ultrasound scan after radiology, while limiting the constraints of environment, transport, time as well as operator skills. Thereby, it is attempted to provide means for further tests accessible in a specialist's medical office or in a non-hospital radiology centre.

Another object of the invention is to provide a means for exploring the endogenous fluorescence, that is a very low signal inside solid organs with a needle having a minimum diameter.

Another object of the invention is to make a fibrous optical probe for the in-depth endogenous fluorescence optical diagnostics of tumours.

DESCRIPTION OF THE INVENTION

The invention provides a device for the in vivo observation or diagnostics by the endogenous fluorescence of a compact biological tissue or living organ, comprising a probe provided with a proximal end on the operator side and a distal end on the side of the tissue to be observed.

According to the invention, this probe comprises:
- a hollow needle ending at the distal end in a cutting point able to penetrate the surface of the tissue to be observed and to sink within said tissue;
- integrally surrounding a single optical fibre the proximal end of which is connected or is arranged to be connected to light injection and recovery means, and the distal end of which has a transverse profile in the continuity of the point of the needle.

The device further comprises:
- light injection and recovery means arranged to inject a so-called feed forward light signal, into the proximal end of the optical fibre, and receive from the distal end of the single optical fibre a so-called feedback light signal of backscattering and of endogenous fluorescence generated by the excitation due to said injected light;
- an analysing device for measuring said feedback signal; and
- optical telemetry means attached to the outer part of said probe and arranged to measure in real time and transmit the sinking depth of said probe within the tissue from a measure of the distance up to the outer surface of said tissue.

Preferably, the optical fibre is of the multimode type, which provides better performances, for example better sensitivity and adjustability.

According to the embodiments, the analysing device can be, for example, a spectrophotometry device as known in the state of the art.

It can also be made by a device only measuring the single strength of the endogenous fluorescence signal, for example to compare it to the strength of the backscattered part of the excitation light.

By sticking the needle into the targeted organ, for example into the breast through the skin, the invention enables the nature of cells located at the point of the needle to be assessed.

This needle has dimensions and characteristics similar to those of standard type needles, preferably the thinnest needles, used for common injections or punctures such as vaccines or blood samples.

It is thus possible to carry out in a simple and local medical context, a first analysis of suspect cells even inside an organ or behind the skin.

In one embodiment, the light injection and recovery means are arranged to be connected to a spectrophotometer arranged to observe the part of the tissue in contact with the distal end of the optical fibre, by measuring at the proximal end of this fibre the backscattering of the injected light and the endogenous fluorescence generated by the excitation due to said injected light.

According to one feature, the analysing device is arranged to be connected to digital computing means arranged to perform an analysis of the strength, duration or wavelength of the backscattered light and of the generated fluorescence, or a combination of all three quantities.

In one embodiment, the light injection means inject a light with a wavelength between near infrared, for example one micrometer or even 1.6 or 2 μm, and near ultraviolet, for example 370 or even 300 or 250 nanometers.

For example, the light injection means comprise at least one laser light source, such as a laser diode at 405 nm, for generating the injected light.

According to another feature, the analysing device is arranged to be connected to digital computing means arranged to perform an analysis of the strength, and possibly the wavelength of the generated fluorescence.

In one preferred embodiment, the light injected means inject a light with a wavelength between 370 and 420 nanometers. The power of the laser diode is selected so that the fibre output power lies at the authorized limit according to the skin laser safety standards.

For example, the light injection means comprise a single laser light source, such as a laser diode at 405 nm, for generating the injected light. This light is focused by an objective lens to the inlet of the fibre after passing through a separating element, for example a cube or a blade.

The feedback signal coming from the same single fibre is collected by the same objective lens which was used for injection, and then redirected to the separating element which sends it back to the analysing device.

In a first alternative, the analysing device comprises an interference filter cutting off the excitation wavelength and passing the higher wavelengths and an objective lens focusing the light onto the inlet of a cooled spectrophotometer.

In a second alternative, the analysing device comprises a dichroic blade, with a separation wavelength slightly higher than that of injected light, separating the signal into two paths. The light of the path corresponding to the wavelength of the injected light is focused on a photodiode, and the light of the path corresponding to the fluorescence wavelengths is focused onto an avalanche photodiode. Both signals are then electronically processed.

Configuration of the Needle

The use of endogenous fluorescence, or auto-fluorescence, as a signal enables the use of specific products enhancing this fluorescence to be avoided, which are often delicate handle products causing undesirable side effects for the patient.

Now this endogenous fluorescence produces by nature a very low signal, which is thus difficult to detect and measure.

A number of existing medical needles for different types of injections have a bevel of 15° or 30°. The 90° angle thus corresponds to a flat end perpendicular to the needle axis.

Preferably, the distal end of the needle and the optical fibre have a transverse profile with a single bevel forming with the axis of the needle an angle between 10° and 25° or even 20°, and in particular 15°. It is to be noted that the meaning "single" bevel corresponds to a bevel with a single main surface, but does not exclude slight side sharpenings of the metal part around the point.

Besides the sharpening, the use of a rather acute angle actually enables the resistance to penetration to be decreased and the pain being caused to be restricted. It also enables a sufficient signal to be recovered in a needle with a minimum diameter as it is necessary to have the greatest interaction area as possible.

According to another feature, the probe further includes a resin gathering in a same continuous tight surface the distal end of the optical fibre with the point of the needle.

Thus the chipping risks of the fibre point are avoided which could then leave particles inside the patient body upon withdrawing the needle.

Preferably, the thinnest needles will be used to reduce pain, that is 23G or 25G needles.

The fibre inside the needle will be preferably a silica fibre, preferably a silica optimized for transmission in the blue and green, for example in the 400-600 nm band, and with a dimension of the core in the order of 200 μm for a 25G needle.

The needle and fibre assembly is thus sufficiently simple and economical to manufacture to be designed as a single use device, which enables the blunting of the sharp edge to be avoided during multiple uses.

Multiple Measurements

Another object of the invention is to provide a device enabling an accurate analysis on an area within the concerned tissues, while limiting the number of perforations, and thus the traumas and pain.

To do so, the invention proposes to perform several measurements during a same perforation operation, step by step on the entire depth explored by the needle.

One object of the present invention is then also to enable a diagnostics signal to be accurately provided at several different depths on the same trajectory.

To do so, the device according to the invention further comprises optical telemetry means attached to the external part of the probe and arranged to measure and transmit the sinking depth of said probe inside the tissue from a measure of the distance up to the external surface of said tissue.

Furthermore, the digital computing means can be arranged to trigger and record a plurality of measures at a plurality of different depths during a movement of the probe along the longitudinal axis of the needle, and to correlate the analysis of this plurality of measures with said plurality of depths.

The probe can thus be used to more easily perform a plurality of measurements at a plurality of different depths during a same introduction of the probe through the skin or the surface of the targeted organ, preferably during extraction. By automatically performing a measurement for each depth pitch during a movement, or an average of several successive ones for each depth, a linear mapping of tissues analysis on the entire sinking depth is obtained. The automatic correlation of the telemetry means with the measurement recording enables the needle to be withdrawn without particular constraint as regard regularity or withdrawal movement rate.

According to one feature, the optical telemetry means comprise at least one pair of juxtaposed optical fibres, among which a first telemetry fibre sends in parallel to the axis of the needle a light beam to the external surface of the tissue to be observed, and a second telemetry fibre recovers the light backscattered by said surface, and is connected to a phototransistor or a photodiode which measures the fraction backscattered by the surface within the luminous flux emitted by the first telemetry fibre, thus providing a measure of the distance to said external surface.

More particularly, the telemetry means can comprise an optical triangulation telemeter, for example laser.

The different above mentioned characteristics can be combined together in different ways, and their different combinations are herein explicitly discussed and specified.

Applications

In typical applications, such as analysis of mammary abnormalities, the invention can be implemented in embodiments where the probe is suitable for use by the outside of the body for the in vivo observation or diagnostics of tissues or organs by sinking through the epidermis.

The probe can thus have dimensions for the outer diameter of the needle 3 and respectively the outer diameter of the fibre 2 lower than 2.10 mm and 1.50 nm respectively, to be compatible with a standard gauge 14 type needle. More particularly, the dimensions of the needle and the fibre could be lower than 1.30 mm and 0.80 mm respectively, that is compatible with a standard gauge 18 or higher type needle.

Dimensions corresponding to the 23G or 25G needles are an interesting solution.

The device enables an in-depth optical diagnostics of tumours to be performed in the cancerology field, with the advantage restricting the invasiveness of the procedure, a good biocompatibility while limiting the implementation time and the operator skills, as well as a limited cost. It is possible for example to contemplate a probe using disposable needles, or a disposable probe per se.

The invention thus allows a method for testing and analysing an area suspected to be a tumour, for example a mammary tumour.

The tumour will be explored for example with an 18 or 23 or higher gauge needle, containing a fibre with a 200 μm core diameter, or even 730 μm or less. The needle will have a length in the order of 10 cm at least to meet the need for mammary exploration. The tumour will be localized during ultrasonography in a similar way to biopsy procedures with a thin needle, and the needle and the optical signal will be used to explore the tumour area and a healthy area for comparison.

A procedure could be to insert the needle through the tumour rapidly to limit pain, and to control the position of the needle during ultrasonography. Then, the needle is slowly removed. The measurements are permanently taken and organized thanks to the telemetry device, for example at a rate of about 5 seconds per centimetre for an acquisition duration of 100 ms to 500 ms. Thus, a special resolution between 0.2 mm and 1 mm will be obtained. Data will be displayed and recorded in real time, at the same time as the ultrasonography video images.

In other applications, it can also be contemplated to implement the invention in embodiments where the probe is adapted for an endoscopic use for the in vivo observation or diagnostics of the inside of tissues or compact organs, by sinking through the envelop of these tissues or organs from a path accessible through endoscopy. It can for example be an embodiment where the probe has dimensions enabling its introduction in the operating channel of an endoscope with its telemetry means located at the outlet of the operating channel. For this, the distance measurement telemetric mode described with two fibres is particularly suitable.

Various embodiments of the invention are provided, integrated according to the whole of their possible combinations different characteristics herein set out.

Further features and advantages of the invention will become clearer from the detailed description of one embodiment in no way limiting, and from the appended drawings wherein:

FIG. 1 is a schematic cross-section view illustrating an embodiment of the invention in an analysis position in a tumour area assumed to be located under the skin;

FIG. 2A is a scheme illustrating the architecture of the light injection and recovery means, in one embodiment of the invention;

FIG. 2B is a scheme illustrating an alternative architecture of the analysing device in an embodiment of FIG. 2A;

FIG. 3 is an experimental chart of strength normalized according to the spectrum, illustrating the validity of results obtained with the optical fibre endogenous fluoroscopy architecture of the invention with respect to those obtained with a confocal microscope;

FIG. 4 is an experimental chart strength according to the spectrum, illustrating the validity of the strength difference detection carried out by the optical fibre endogenous fluoroscopy architecture of the invention by comparison between the results obtained for a tumour tissue and a healthy tissue;

FIG. 5 is an experimental chart of strength normalized according to the spectrum, illustrating the validity of the spectral shifting detection performed by the optical fibre endogenous fluoroscopy architecture of the invention by comparison between the results obtained for a tumour tissue and a healthy tissue;

FIG. 6 is an experimental chart of strength normalized according to the spectrum, illustrating the background noises obtained in a healthy tissue with the sharpened fibre and needle architecture compared with those obtained with the upright end single fibre architecture;

FIG. 7 is an experimental chart of strength according to the spectrum, illustrating the results obtained in a tumour tissue with the sharpened fibre and needle architecture compared with those obtained with the upright end single fibre architecture.

DESCRIPTION OF THE FIGURES

In the embodiment illustrated in FIG. 1 and FIGS. 2A and 2B, the probe 10 of the device according to the invention comprises at its distal end 11 an optical fibre 2 included in a hollow needle 3 ending in a cutting point 4. The fibre is bonded in the hollow of the needle and polished at its distal end 21 so as to take on the exact cutting shape of the point 4 of the needle. The polishing angle of the distal end 21 of the optical fibre 2 corresponds to that of the sharp point 4 of the needle.

A light injection and recovery device 6 placed at the proximal inlet 22 of the fibre injects a feed forward light signal 601, the tissue 91 located at the distal end of the needle and of the fibre sends back a feedback light signal 602 of backscattering and (endogenous) fluorescence into the fibre 2. This feedback signal 602 is transmitted by the fibre 2 to the light injection and recovery device 6 which analyses it, in particular in strength and wavelength. An optical telemeter 7 placed on the outside of the proximal tip 1 of the needle measures the distance D7 to the skin and enables the depth P10 of the explored area 91 to be deduced.

Figure 2A:
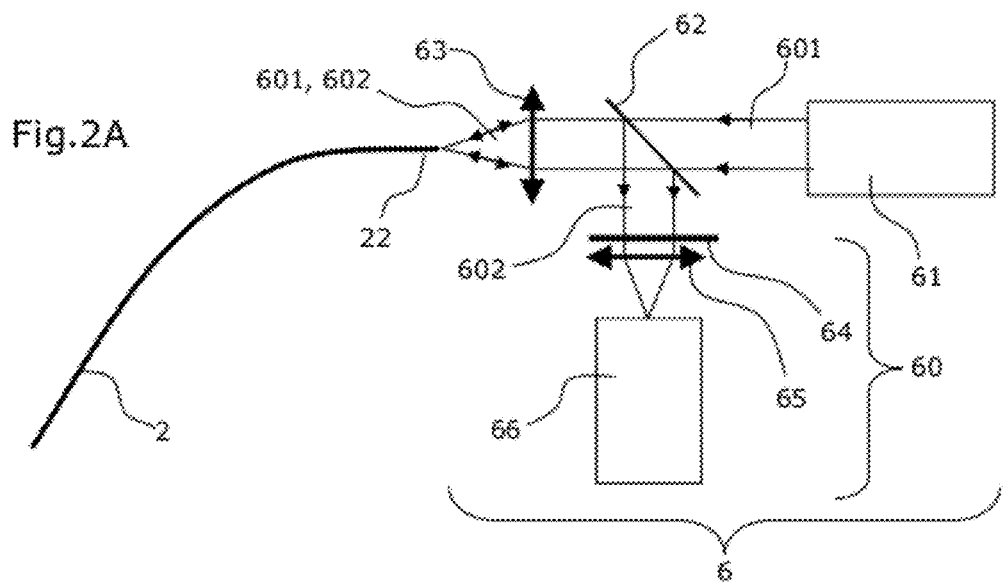

In the embodiment illustrated in FIG. 2A, the light injection and recovery device 6 comprises a light source 61 focalized on the inlet 22 of the fibre 2 through a separating blade 62, which recovers the feedback signal 602 and sends it back to a spectrophotometer 66 analysing the feedback signal in strength and wavelength, or even in duration.

The light 601 injected into the fibre 2 lies in the wavelength range between near infrared and near ultraviolet and can comprise one or more continuous or pulsed laser sources.

In particular for the observation by the endogenous fluorescence, the injected light lies preferably between 370 and 420 nanometers.

Figure 2B:
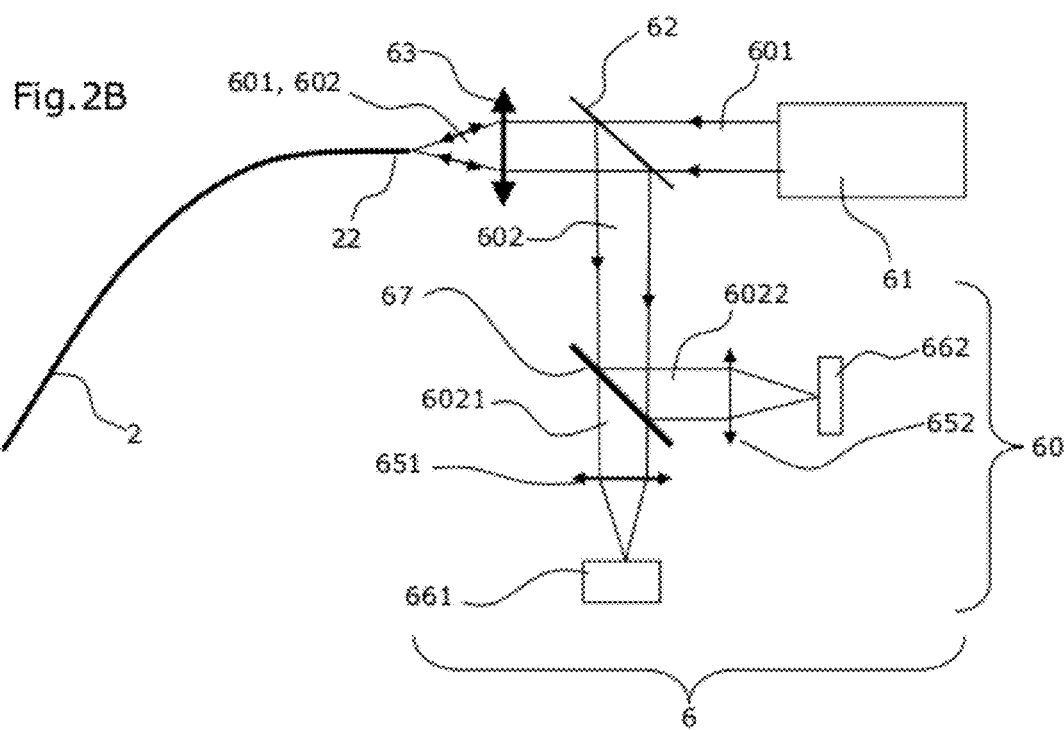

In one alternative illustrated in FIG. 2B, the analysing device 60 comprises separating means according to the wavelength (herein a dichroic blade) 67, with a separation wavelength being 5 to 30 nm higher than that of the injected light (that is for example a separation wavelength of 420 nm), provided to separate part or all of the feedback signal 602 into two paths:
- a first path (6021) is formed which comprises light corresponding to the wavelengths of the endogenous fluorescence of the observed tissues 91 (here the light that has passed through the dichroic blade 67), and then is focused by an objective lens (here a lens 651) on a first photodetector, here an avalanche photodiode 661; and
- a second path (6022) wherein the light corresponds to the length of the injected light 601 (here the light reflected by the dichroic blade) and is focused by an objective lens (652) onto a second photodetector, for example a photodiode 662.

Both signals are then electronically processed and compared by computing and/or representation means.

By thus filtering the feedback signal 602 according to its wavelength, it is possible to measure the endogenous fluorescence by measuring its strength only, here in the avalanche diode 661, which can then be compared to the excitation strength measured by the photodiode 662 of the second path. Is obtained in particular a simple compact robust analysing device 60, able to be made with a few cheap components; and well adapted to the quick signal fluctuations when the needle penetrates the skin.

In order to mark the depth of the needle, the optical telemeter 7 located at the base 1 of the needle 3 comprises a pair of juxtaposed telemetry optical fibres (not represented). A first telemetry fibre sends a light beam 71 into the axis A3 of the needle 3. A second telemetry fibre recovers the light backscattered by the skin or the surface 90 of the organ 9. At the proximal end of the second telemetry fibre, a detector such as for example a phototransistor measures the flux fraction 71 which is backscattered by the skin 90, which enables the distance D7 between the skin 90 and the telemeter 7 and/or the variation in this distance D7 to be assessed. The variation in this distance D7 allows the device to measure and record the sinking depth P10 of the probe inside the explored tissue 9.

According to an alternative of the telemeter, not represented here, the optical telemeter located at the base of the needle comprises an optical triangulation telemeter, that can be made according to different technologies such as for example with a conventional LED or laser.

According to an embodiment, the probe device 1 comprises a single optical fibre 2 with a 736 μm outer diameter (approximately), 300 μm core diameter and 0.22 numerical aperture. This fibre is inserted in the hollow of an 18G ("18 gauge") type needle 3, with a cutting point 4 having a sharp edge tilted at 15°.

Preferably, according to another embodiment, the optical fibre 2 has a 250 μm outer diameter, 200 μm core diameter and 0.22 numerical aperture. It is inserted in the hollow of a "25G gauge" type needle 3, with a cutting point 4 having a sharp edge tilted at 15°.

The fibre 2 is inserted and bonded in the hollow of the needle 3 with epoxy glue. It is then polished so as to take on the exact sharp shape of the needle end. A thin epoxy glue layer, for example transparent, is left on the surface, possibly only on the perimeter of the fibre, which fills in the spaces and will prevent chipping of the angles of the fibre end.

The tissue or organ 9 to be explored is pricked by the needle 3, until the needle pass through the tumour 5 to be analysed.

The light injection and recovery device 6 placed at the inlet of the fibre 2 consists of a light source 61 sending a collimated beam 601 passing through the separating blade 62 and then converging onto the inlet face of the proximal end 22 of the fibre 2, after passing through the first objective lens 63. The feedback light 602 sent back by the tumour passes again through the first objective lens 63 and then is deviated by the separating blade 62 to a filter 64 attenuating the wavelength emitted by the source 61, and then is injected thanks to a second objective lens 65 to the spectrophotometer 66.

By way of non-limiting example, the light source 61 can comprise or consist of a laser diode collimated at 405 nm with 20 mW power, the separating blade 62 of the separating cube, the objective lens 63 and 65 of ×10 microscope objectives, the filter 64 of a high-pass filter with a 420 nm cut-off wavelength, the spectrophotometer 66 of a CCD strip fibrous spectrophotometer cooled by Peltier effect.

The part 91 of the tissue 5 or 9 located at the distal end 21 and 4 of the fibre 2 and the needle 3 backscatters the incident light 601 into the fibre. It is further excited by the same incident light 601, which further generates a fluorescence signal, part of the flux of which is recovered by the distal end 21 of the fibre 2. The light 602 sent back to the injection and recovery device 6 is analysed, in particular in strength, duration and wavelength by the spectrophotometer 66. The result of this analysis, or of calculations performed from part or all of these quantities, enable the material explored in-depth to be diagnosed without sampling.

This diagnostics is based on specificities in strength, spectrum and duration of the tumour signal forming a signature called tumour signature, the characteristics of which have been studied and evaluated by the inventors, as described hereinafter.

An optical telemeter 7 is placed onto the outer tip, that is the proximal part of the needle 3, and measures the distance D7 from the needle tip to the skin 90. The length D3 of the needle 3 being known, it allows computing means (not represented) to know the depth P10 of the explored area, and to provide and record the marked signals each according to its depth.

The needle is quickly sunk to worsen pain, and then gently removed, the more slowly it is removed, the better the spatial resolution of the measurement. At each point, the depth of the explored area is known thanks to the telemeter. By way of non-limiting examples, the diagnostics signal can consist of the global fluorescence strength generated by an excitation at 405 nm, of the spectrum shape and/or the strength backscattered at 405 nm.

Results of the Spectral Signature

The inventors have tested a prototype corresponding to the embodiment described herein, to validate the results obtained with this type of architecture and at 405 nm.

Figure 3:
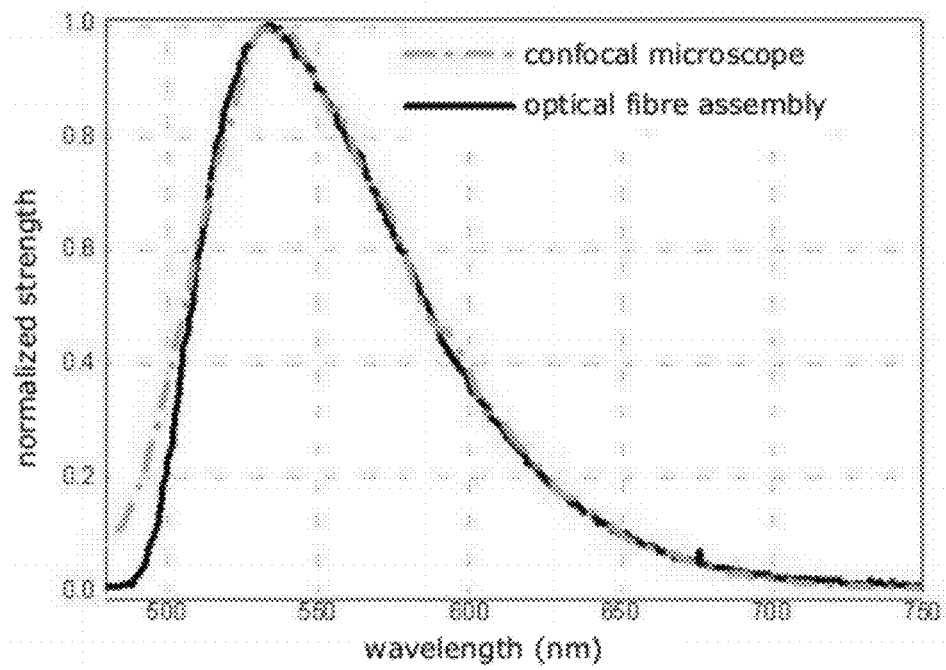

The chart of FIG. 3 represents the strength normalized with the optical fibre endogenous fluoroscopy architecture of the invention, on a spectral range from 480 nm to 750 nm, compared with the results of a confocal microscope, which is frequently a bench mark in this field. The similarity of both curves shows that the architecture of the device according to the invention gives results very close to the confocal microscope, which is favourable for the validity of analyses that could be deduced therefrom.

Figure 4:
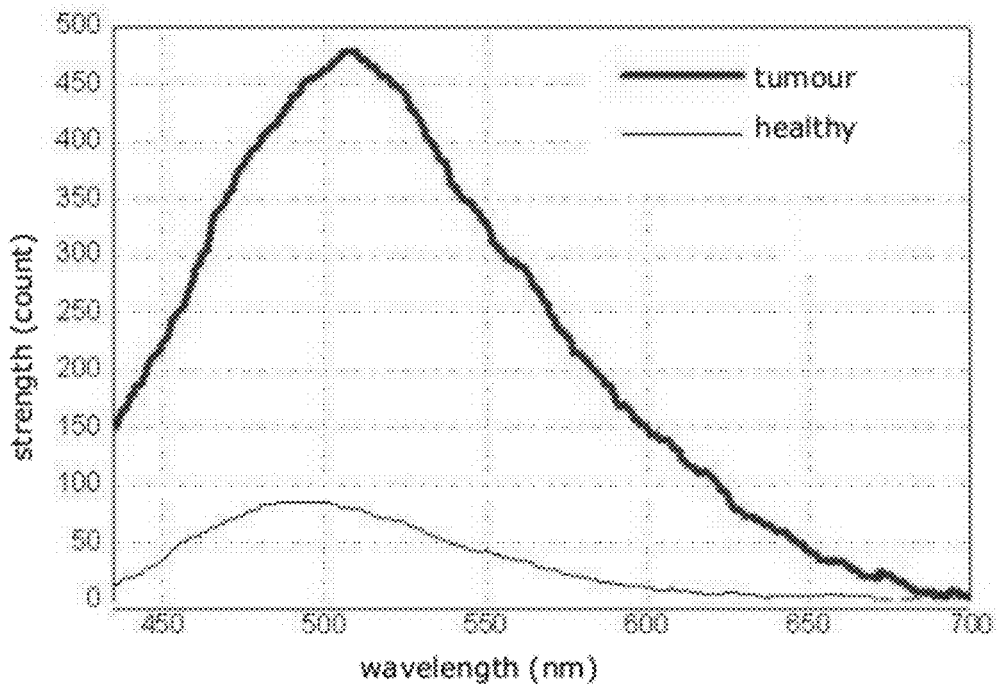

The chart of FIG. 4 represents the fluorescence strength obtained by the device according to the invention on a spectral range from 430 nm to 700 nm, on average for ten measures on an established tumour sample (top thick curve) in comparison with a healthy sample (bottom thin curve). The strength about the 510 nm peak is about five times higher for the tumour sample, and thereby is a robust differentiation criterion usable to make up an analysis or even a diagnostics thanks to the device according to the invention.

Figure 5:
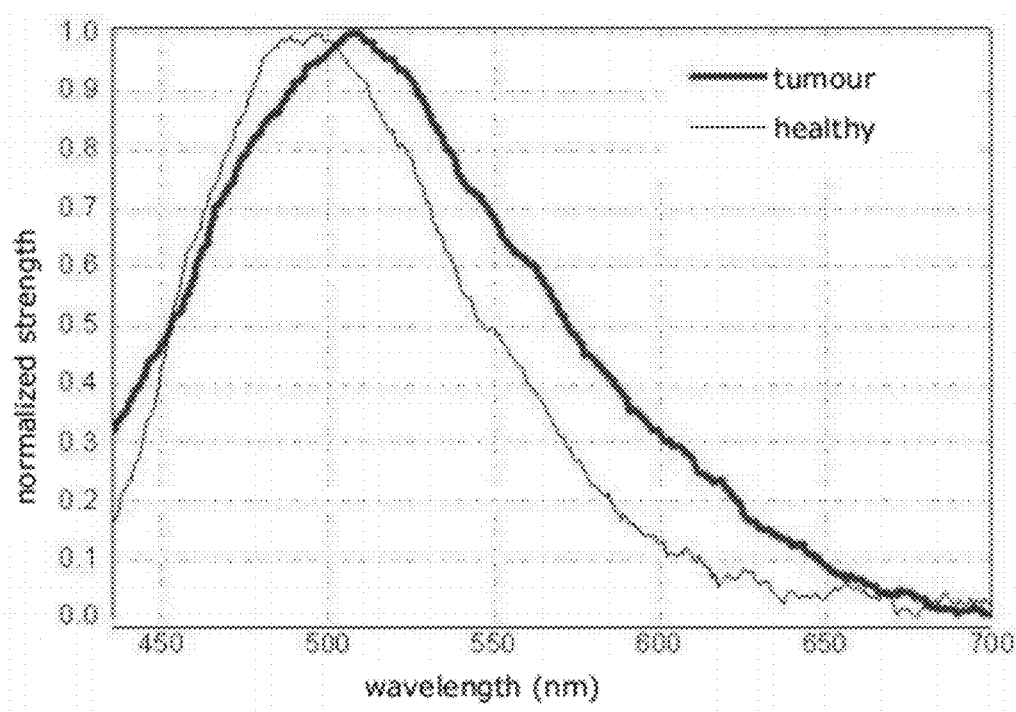

The chart of FIG. 5 represents the strengths of FIG. 4 after strength normalization. This normalization enables to see among other things a spectral shifting to red ranging from 10 nm to 25 nm. This spectral shifting is another differentiation criterion usable to make up an analysis or even a diagnostics thanks to the device according to the invention.

Both these criteria thus appear to be particularly interesting, together or separately, in combination with the architecture herein described.

The device according to the invention can thus comprise digital computing means programmed or arranged to compute either criterion or a combination of these criteria. The apparatus can then deduce an analysis, for example a numbered one or a linear graphical representation, or even compare them to a diagnostic table to put forward a diagnostics or a diagnostic assistance.

Performances of the Bevelled Probe

From the evaluation of the spectral signature, the inventors have more accurately studied the results obtained with a sharpened probe integrated in a needle according to the invention, by comparing it with the configuration of a needleless optical fibre and the distal end of which has an upright surface, that is at 90° or perpendicular to the axis of this fibre.

Figure 6:
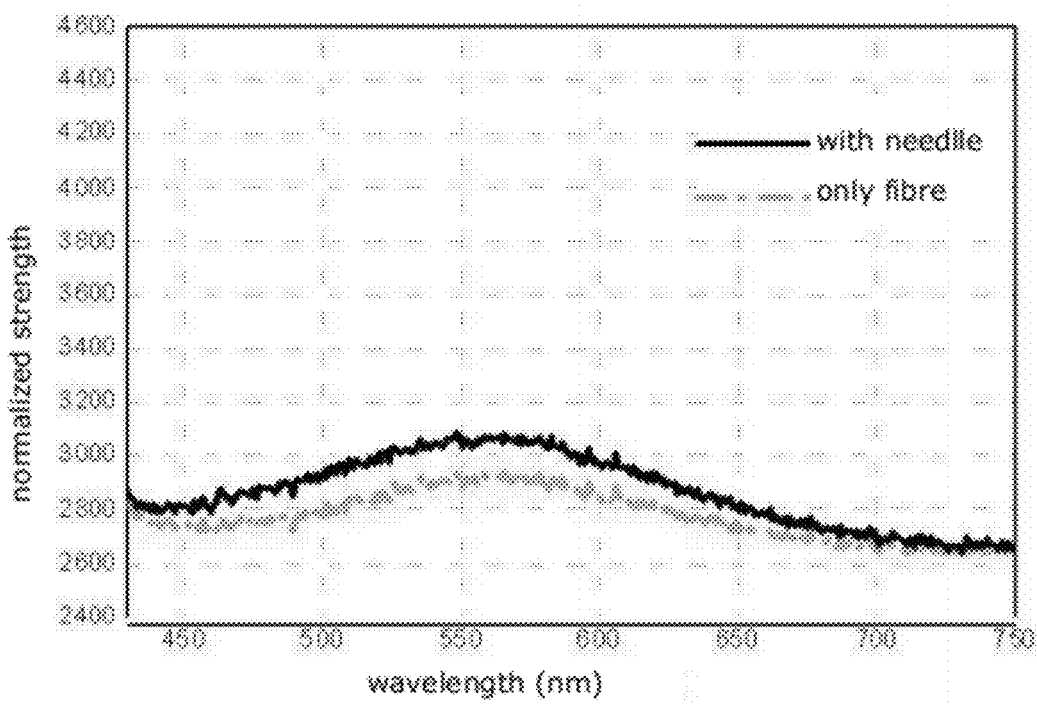

The chart of FIG. 6 represents the strength obtained in water by the device according to the invention on a spectral range from 430 nm to 750 nm, compared with an assembly with a dark fibre having a distal end at 90°.

Figure 7:
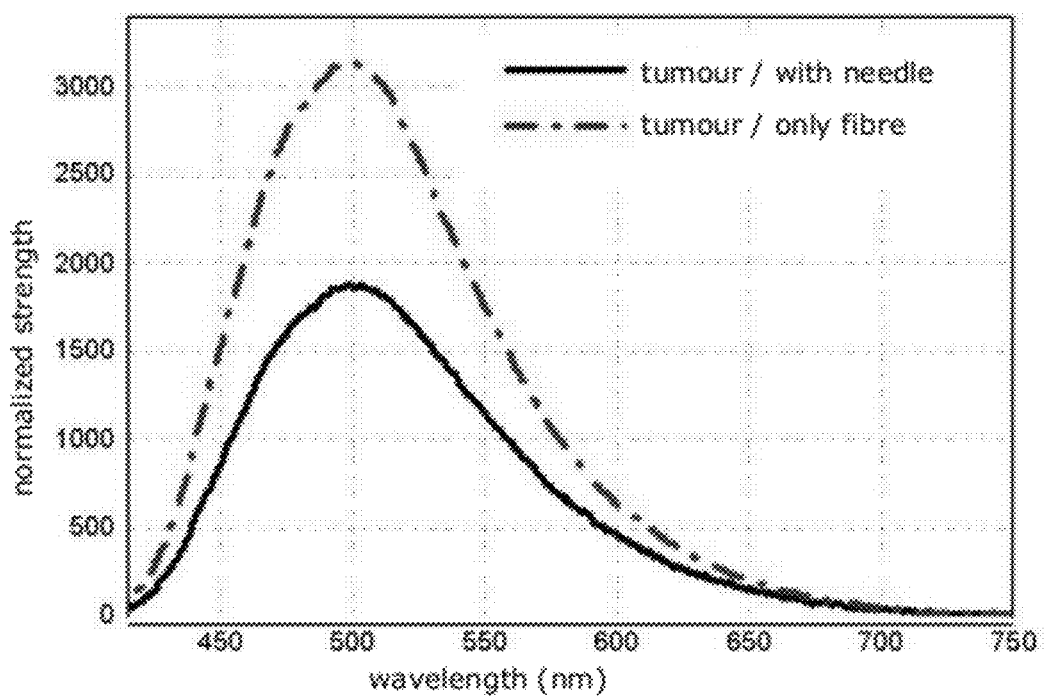

The chart of FIG. 7 represents the strength obtained by the device according to the invention on the same spectral range after subtracting the background noise, for a tumour sample, compared with an assembly with a single fibre having a distal end at 90°. This figure shows that the shape of signals measured in a human tissue sample is unchanged regardless of the probe used, with an attenuation factor of about two.

The experimentation shows that the signal of the fibre polished at 15° under a needle is sufficiently strong to be detected, and thereby can be used for the application contemplated.

These results have been obtained with a power calculated to meet the security criteria for in vivo use of laser. These criteria depend on the contact area of the distal end of the fibre with the tissues to be explored but using a bevel increases this area. It is thereby possible to increase the laser power, and partly make up for the decrease in the signal observed with the fibre bevelled under a needle.

The signal to noise ratio (signal amplitude/noise amplitude) for single measurements is between 6 and 9 for an acquisition duration of one second, which provides sufficiently significant results to contemplate the possibility of a step by step measurement.

The experimentation thus seems to confirm the efficiency of the measurement architecture with a sharpened fibre and under a needle as described herein, more particularly in combination with the light injection and recovery device, for example using either or both strength or spectral shifting criteria.

Of course, the invention is not limited to the examples just described and numerous changes can be provided to these examples without departing from the scope of the invention.

The invention claimed is:

1. A device for in-depth in vivo observation or diagnostics of a compact biological tissue or a living organ, in particular a tumor, comprising:
   a probe provided with a proximal end on an operator side and a distal end on the side of the tissue to be observed or diagnosed, and comprising a hollow needle ending at the distal end in a cutting point able to penetrate a surface of the tissue to be observed or diagnosed and to sink within said tissue, wherein the needle includes and integrally surrounds a single optical fiber of the multimode type, the distal end of which has an exact cutting shape of the distal end of the needle and in the continuity of the cutting point of the needle, the distal end of the needle and of the optical fiber having a tapering profile with a single bevel forming an angle with the longitudinal axis of the needle, the angle being between 10° and 25°, wherein the needle surrounds the optical fiber except on the single bevel; and
   a light injection and recovery means connected to a proximal end of said optical fiber and arranged to inject a feed forward, continuous, low energy light signal into the proximal end of the optical fiber and to receive out of the proximal end of said optical fiber at least one feedback light signal of endogenous fluorescence generated by excitation due to said injected light, said feedback light signal being collected through said bevel of said optical fiber;

wherein the light injection and recovery means comprises an analyzing device for measuring said feedback signal, said analyzing device comprising separating means that separate said feedback signal according to a wavelength regardless of time, thus obtaining a steady-state spectral analyzing.

2. The device according to claim 1, wherein the light injection and recovery means injects a light with a wavelength between 370 and 420 nanometers.

3. The device according to claim 1, wherein the light injection and recovery means comprises a laser light source for generating the light to be injected;

A separating element through which the light from the light source passes; and

An objective lens to focus the light to inside the optical fiber after passing through the separating element:

wherein the feedback light signal coming from the single optical fiber is collected by the objective lens, and then redirected to the separating element which sends the feedback light signal to the analyzing device.

4. The device according to claim 3, wherein the laser light source is a laser diode at 405 nm.

5. The device according to claim 1, wherein the analyzing device comprises an interference filter cutting off a wavelength of the injected light and passing higher wavelengths, and an objective lens focusing at least part of the feedback light signal onto an inlet of a cooled spectrophotometer.

6. The device according to claim 1, wherein the separating means has a separating wavelength 5 to 30 nm higher than that of the injected light, to separate at least part of the feedback light signal into:

a first path comprising light which corresponds to wavelengths of the endogenous fluorescence of the observed tissues and is focused by an objective lens onto a first photodetector; and a second path comprising light which corresponds to wavelength of the injected light and is focused by an objective lens onto a second photodetector.

7. The device according to claim 1, wherein the probe comprises a needle having dimensions equal to or lower than dimensions of 23 gauge needles.

8. The device according to claim 1, wherein the fiber within the needle is a silica fiber, optimized for transmission in a blue green spectrum and with a core in the order of 200 gm.

9. The device according to claim 1, further comprising optical telemetry means which are attached to an outer part of the probe and arranged to measure and transmit a sinking depth of said probe into the tissue, from a measure of a distance up to an outer surface of said tissue.

10. The device according to claim 9, wherein the optical telemetry means comprises at least one pair of juxtaposed optical fibers, among which a first telemetry fiber sends in parallel to the longitudinal axis of the needle a light beam to the outer surface of the tissue to be observed, and a second telemetry fiber recovers the light backscattered by said surface and is connected to a phototransistor or a photodiode which measures a fraction backscattered by the surface within a luminous flux emitted by the first telemetry fiber, thereby providing a measure of the distance up to said outer surface.

11. The device according to claim 9, wherein the optical telemetry means comprises an optical triangulation telemeter.

12. The device according to claim 9, wherein the probe is adapted to be introduced into an operating channel of an endoscope with the telemetry means located at a distal outlet of the operating channel, for in vivo observation or diagnostics of inside of compact tissues or organs by sinking through an envelope of said tissues or organs from a path accessible through endoscopy.

13. The device according to claim 12, wherein digital computing means are arranged to trigger and record a plurality of measures at a plurality of different depths during a movement of the probe along the longitudinal axis of the needle, and to correlate the analysis of the plurality of measures with said plurality of depths.

14. The device according to claim 1, wherein the light injection and recovery means has a power of 20 mW.

15. A device for in-depth in vivo observation or diagnostics of a compact biological tissue or a living organ, in particular a tumor, comprising:

a probe provided with a proximal end on an operator side and a distal end on the side of the tissue to be observed or diagnosed, and comprising a hollow needle ending at the distal end in a cutting point able to penetrate a surface of the tissue to be observed or diagnosed and to sink within said tissue, wherein the needle includes and integrally surrounds a single optical fiber bonded in the hollow of the needle so as to be integrally surrounded by the metallic wall of the needle in a uniform manner, said fiber being of the multimode type, the distal end of which has an exact cutting shape of the distal end of the needle and in the continuity of the cutting point of the needle, the distal end of the needle and of the optical fiber has a tapering profile with a single bevel forming an angle with the longitudinal axis of the needle, the angle being between 10° and 25°, wherein the needle surrounds the optical fiber except on the single bevel; and a light injection and recovery means connected to a proximal end of said optical fiber and arranged to inject a feed forward, continuous, low energy light signal into the proximal end of the optical fiber and to receive out of the proximal end of said optical fiber at least one feedback light signal of endogenous fluorescence generated by excitation due to said injected light, said feedback light signal being collected through said bevel of said optical fiber;

wherein the light injection and recovery means comprises an analyzing device for measuring said feedback signal, said analyzing device comprising separating means that separate said feedback signal according to a wavelength, regardless of time, thus obtaining a steady-state spectral analyzing.

16. The device according to claim 15, wherein the light injection and recovery means has a power of 20 mW.

* * * * *